(12) United States Patent
Clawson et al.

(10) Patent No.: US 6,363,930 B1
(45) Date of Patent: Apr. 2, 2002

(54) APPARATUS FOR PROVIDING HEAT/MOISTURE TO RESPIRATORY GASES

(75) Inventors: Burrell E. Clawson, Newport Beach, CA (US); James Weigl, Las Vegas, NV (US)

(73) Assignee: Enternet Medical, Inc., Las Vegas, NV (US)

( * ) Notice: Subject to any disclaimer, the term of this patent is extended or adjusted under 35 U.S.C. 154(b) by 0 days.

(21) Appl. No.: 09/113,229

(22) Filed: Jul. 10, 1998

(51) Int. Cl.$^7$ ............................................. A62B 18/08
(52) U.S. Cl. ........................ 128/201.13; 128/205.12; 128/203.16
(58) Field of Search ............... 128/201.13, 203.12, 128/205.25, 205.26, 205.27, 205.28, 205.29, 205.12, 203.16, 204.13, 206.16

(56) References Cited

U.S. PATENT DOCUMENTS

| | | | |
|---|---|---|---|
| 3,612,048 A | * 10/1971 | Taheeda | 128/205.28 |
| 3,615,233 A | * 10/1971 | Doering et al. | 128/205.28 |
| 3,721,238 A | 3/1973 | Wise et al. | |
| 3,747,598 A | 7/1973 | Cowans | |
| 3,782,081 A | 1/1974 | Munters | |
| 3,912,795 A | * 10/1975 | Jackson | 128/203.12 |
| 3,932,153 A | 1/1976 | Byrns | |
| 5,577,494 A | 11/1976 | Kuypers et al. | |
| 4,036,616 A | 7/1977 | Byrns | |
| 4,063,913 A | 12/1977 | Kippel et al. | |
| 4,090,513 A | 5/1978 | Togawa | |
| 4,108,172 A | 8/1978 | Moore, Jr. | |
| 4,133,656 A | 1/1979 | Kippel et al. | |
| 4,148,732 A | 4/1979 | Burrow et al. | |
| 4,168,706 A | 9/1979 | Lovell | |
| 4,171,962 A | 10/1979 | Kippel et al. | |
| 4,172,709 A | 10/1979 | Kippel et al. | |
| 4,181,511 A | 1/1980 | Kippel et al. | |
| 4,181,512 A | 1/1980 | Kippel et al. | |
| 4,200,094 A | 4/1980 | Gedeon et al. | |
| 4,224,939 A | 9/1980 | Lang | |
| 4,297,117 A | 10/1981 | Holter et al. | |
| 4,360,018 A | 11/1982 | Choksi | |
| 4,367,734 A | 1/1983 | Benthin | |
| 4,458,679 A | 7/1984 | Ward | |
| 4,516,573 A | 5/1985 | Gedeon | |
| 4,597,917 A | 7/1986 | Lunsford | |
| 4,707,167 A | 11/1987 | Saito et al. | |
| 4,771,770 A | 9/1988 | Artemenko et al. | |
| 4,829,997 A | 5/1989 | Douwens et al. | |
| 5,016,628 A | 5/1991 | Lambert | |
| 5,022,394 A | 7/1991 | Chmielinski | |

(List continued on next page.)

FOREIGN PATENT DOCUMENTS

GB 322790 * 12/1929 ............ 128/201.13

Primary Examiner—John G. Weiss
Assistant Examiner—V. Srivastava
(74) Attorney, Agent, or Firm—Stout, Uxa, Buyan & Mullins, LLP; Frank J. Uxa

(57) ABSTRACT

Apparatus for heating and humidifying respiratory gases include a housing, a filter element located in the housing, and a gas permeable member positioned in the housing to exchange heat and moisture with respiratory gases passing through the housing. In one embodiment, the inlet portion of the housing is detachably secured to the remainder of the housing and is adapted to be replaced, together with the filter element, while the outlet portion of the housing remains connected to the tube for passing respiratory gases. Additional materials, such as generating material useful to produce moisture and heat and heat generating materials useful to generate heat may be included within the housing. The present apparatus are particularly structured and adapted to reduce the risk of causing trauma to the patient and to increase the safety and comfort of the patient using such apparatus.

14 Claims, 6 Drawing Sheets

U.S. PATENT DOCUMENTS

| | | | |
|---|---|---|---|
| 5,035,236 A | | 7/1991 | Kanegaonkar |
| 5,038,767 A | | 8/1991 | Jumpertz |
| 5,109,471 A | | 4/1992 | Lang |
| 5,172,686 A | | 12/1992 | Anthony |
| 5,195,527 A | | 3/1993 | Hicks |
| 5,213,096 A | | 5/1993 | Kihlberg et al. |
| 5,228,435 A | | 7/1993 | Smith |
| 5,230,727 A | | 7/1993 | Pound et al. |
| 5,255,674 A | | 10/1993 | Oftedal et al. |
| 5,320,096 A | | 6/1994 | Hans |
| 5,333,607 A | | 8/1994 | Kee et al. |
| 5,337,739 A | | 8/1994 | Lehman |
| 5,349,946 A | * | 9/1994 | McComb ............... 128/203.17 |
| 5,360,002 A | | 11/1994 | Smith |
| 5,383,447 A | | 1/1995 | Lang |
| 5,386,825 A | | 2/1995 | Bates |
| 5,390,668 A | | 2/1995 | Lehman |
| 5,435,298 A | | 7/1995 | Anthony |
| 5,435,299 A | | 7/1995 | Langman |
| 5,460,172 A | | 10/1995 | Eckerbom et al. |
| 5,462,048 A | | 10/1995 | Lambert et al. |
| 5,468,451 A | | 11/1995 | Gedeon |
| 5,482,031 A | | 1/1996 | Lambert |
| 5,487,382 A | | 1/1996 | Bezicot |
| 5,505,768 A | | 4/1996 | Altadonna |
| 5,546,930 A | | 8/1996 | Wikefeldt |
| 5,558,088 A | | 9/1996 | Smith |
| 5,570,684 A | | 11/1996 | Behr |
| 5,590,644 A | | 1/1997 | Rosenkoetter |
| 5,640,952 A | * | 6/1997 | Susann et al. ......... 128/204.18 |
| 5,647,344 A | | 7/1997 | Turnbull |
| 5,660,173 A | * | 8/1997 | Newton ................. 128/286.17 |
| 5,992,413 A | | 11/1999 | Martin, Jr. et al. |

\* cited by examiner

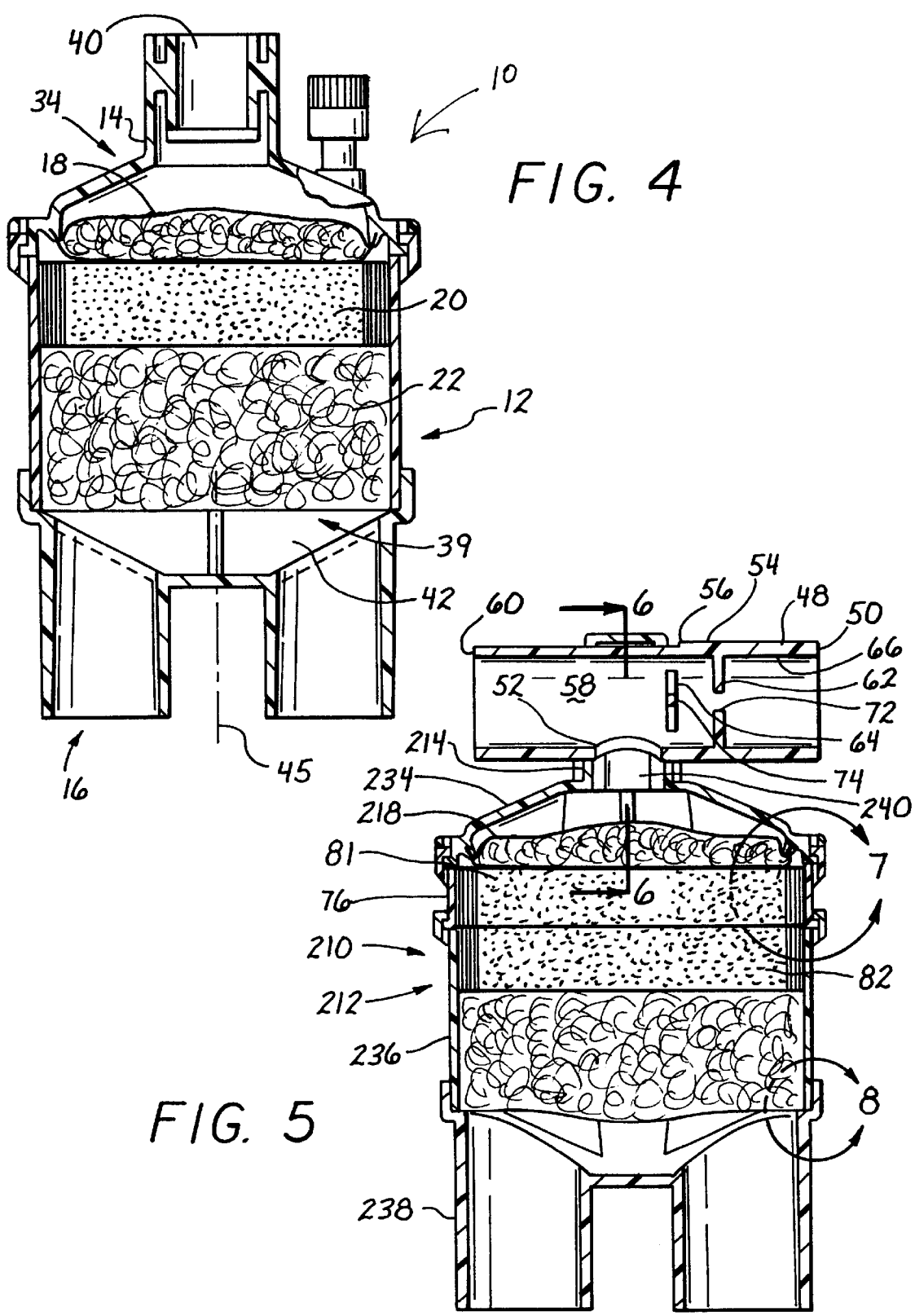

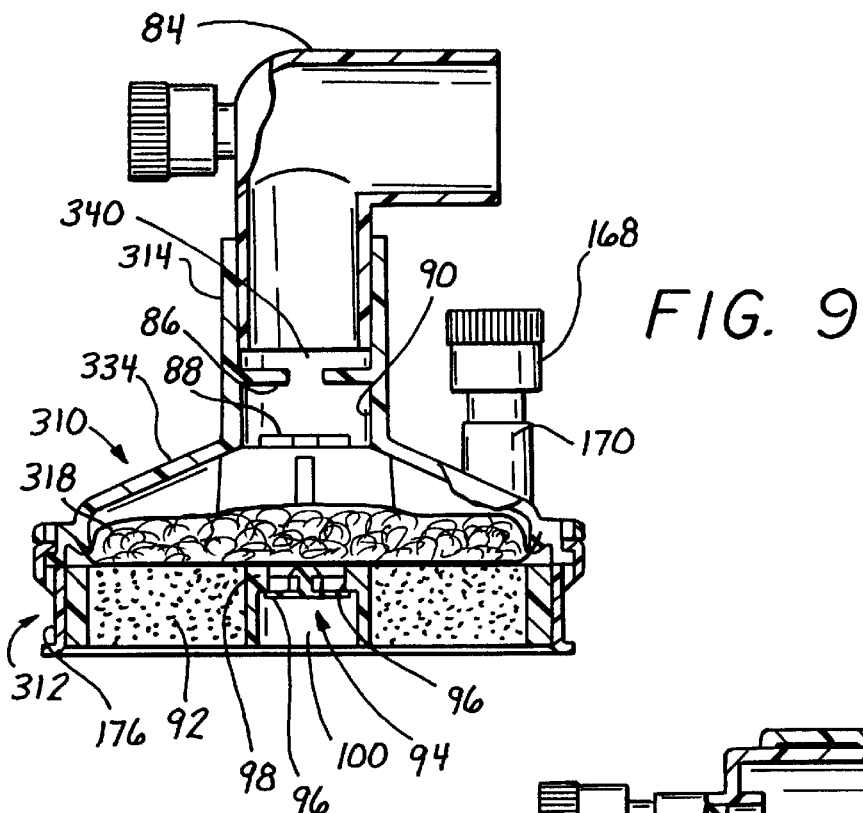
FIG. 9
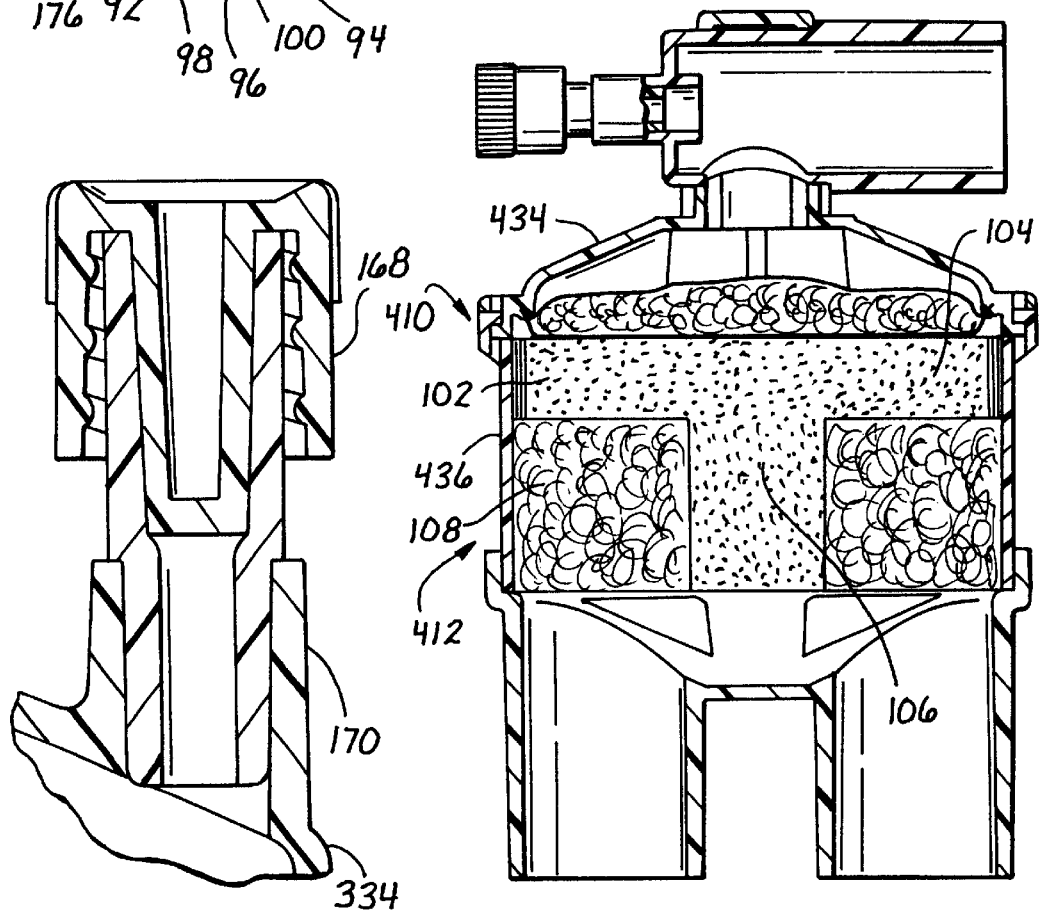
FIG. 11
FIG. 10

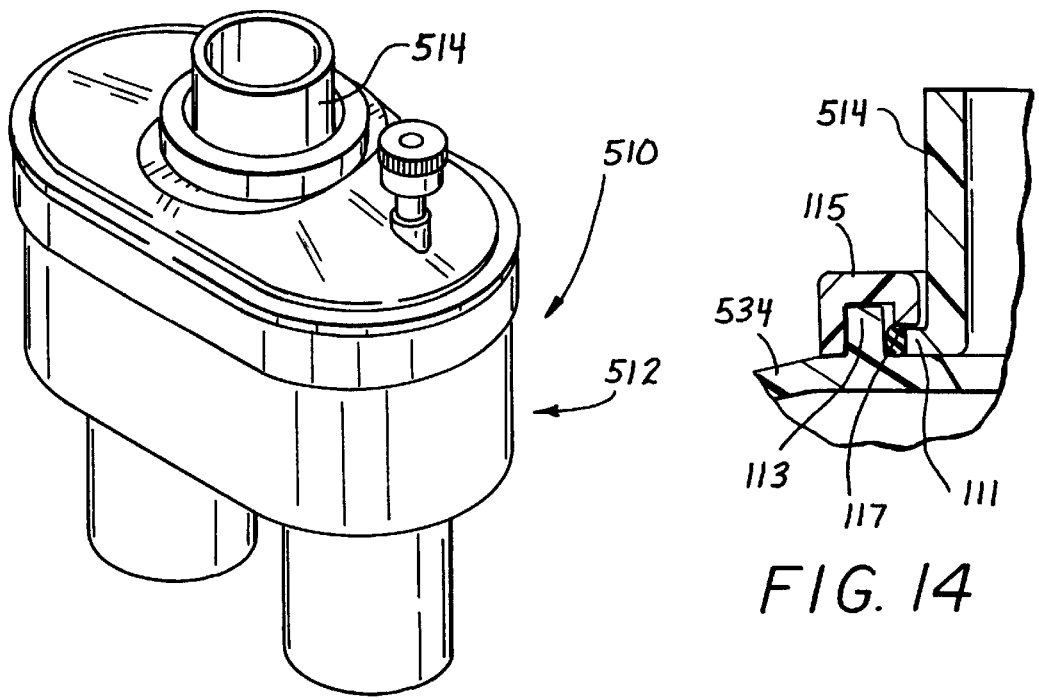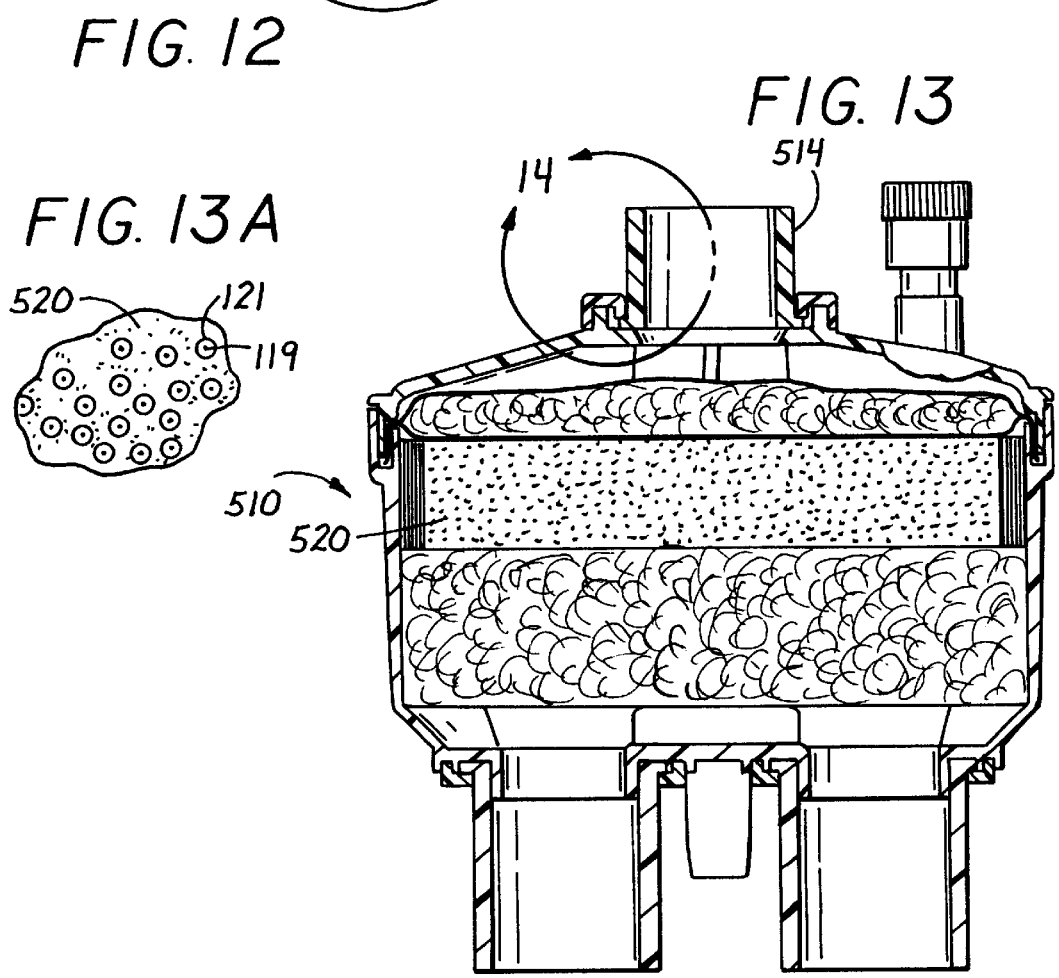

APPARATUS FOR PROVIDING HEAT/MOISTURE TO RESPIRATORY GASES

BACKGROUND OF THE INVENTION

The present invention relates to apparatus useful to exchange heat and moisture in respiratory gas applications. More particularly, the invention relates to apparatus for heating and humidifying respiratory gases which exchange heat and moisture with respiratory gases, and preferably provide, e.g., generate, additional heat and/or moisture available to the respiratory gases.

During surgery and other medical procedures, a patient is frequently connected to an anesthesia machine or ventilator to provide respiratory gases to the patient. The respiratory gases passed to the patient are advantageously heated and humidified so that the gases entering the patient are of a suitable temperature and humidity so as not to adversely impact the patient. Heat and moisture exchangers (HMES) are often used to provide heat and humidity to the respiratory gases entering the patient. Typically, these HMEs are located so that respiratory gases from the patient pass through a tracheal tube into the HME, often a fibrous or other gas permeable material, which accumulates or collects heat and moisture from the exhaled gases. During the inhaling of respiratory gases, for example, from an anesthesia machine, the HME provides both heat and moisture to these respiratory gases prior to the gases entering the patient. Over a period of time, the HME is effective to maintain a certain level of temperature and humidity in the respiratory gases entering the patient.

Such HMEs do, however, have certain drawbacks. Thus, standard HME units currently commercially available are often less than satisfactory in delivering heat and/or moisture to the patient, for example, during the initial operation of the unit, and have configurations and structures which can cause clinician anxiety and patient trauma, for example, when the patient or HME unit is moved and the like situations. Also, during the initial or start up phase of the operation of a HME member, the amount of heat and moisture being exchanged out of the HME member to the respiratory gases being passed back to the patient is relatively low, for example, because the HME member is at a reduced temperature and a reduced moisture content. This "start up" problem can adversely affect the patient. One approach to overcoming at least a portion of this problem is to provide the HME member with a hygroscopic component, for example, calcium chloride and the like components, which is effective to generate a limited amount of heat as the exhaled gases leaving the patient pass through the HME member. This provides a "quick warm up" HME member and at least provides a heated respiratory gas stream to the patient relatively quickly. However, the degree of humidification of the respiratory gases being passed to the patient still is relatively low during the first portion of the HME member operation, in part because of the water held by the hygroscopic component.

In addition, the inefficiencies of the typical HME member are such that a certain portion of the heat and moisture collected by the HME is lost, for example, to the environment, rather than being passed back to the patient by exchange with respiratory gases. The degree of heating and/or humidification of the respiratory gases varies over time which can adversely impact the patient.

In short, although the current commercial HME units provide certain benefits, they are not very user friendly to the patient.

It would be advantageous to provide apparatus by which respiratory gases can be effectively and reliably heated and humidified so that the comfort and safety of the patient is enhanced.

SUMMARY OF THE INVENTION

New apparatus for heating and humidifying respiratory gases have been discovered. Such apparatus provide for exchanging heat and moisture with respiratory gases exhaled by the patient and providing heat and moisture to the respiratory gases being inhaled by the patient. In general, the present apparatus are more patient friendly, that is provide for increased comfort and/or reduced trauma to the patient undergoing surgery or other treatment, than the current commercially available HMEs. Various features of the present invention provide enhancements as to the comfort and safety of the patient. Thus, the use of the present apparatus effectively provides heat and moisture to respiratory gases with reduced, if any, adverse effects on the patient. One important feature of the present apparatus is enhanced start up effectiveness so that the "warm up" or "break in" time period of the system is reduced or even eliminated. These benefits are obtained with apparatus which are straightforward in construction, easy and relatively inexpensive to manufacture and use, and are effectively controlled to provide the results desired.

Generally, the present invention is directed to apparatus for heating and humidifying respiratory gases.

In one broad aspect of the present invention, apparatus for heating and humidifying respiratory gases comprise a housing, a filter element, and a gas permeable member. The housing has an inlet adapted for connection to a tracheal tube device and an outlet adapted for connection to a tube or tubes for passing respiratory gases, for example, to and from an anesthesia machine, ventilator and the like. The inlet and the outlet are positioned so that respiratory gases passing through the housing pass therebetween. The filter element is located in the housing and is adapted to filter respiratory gases passing through the housing. The gas permeable member is positioned in the housing between the inlet and the outlet and is adapted to exchange heat and moisture with respiratory gases passing through the housing. In general, the housing is designed to be compact and to reduce the amount of dead space between the tracheal tube device and the tube (or tubes) for passing respiratory gases. The compact housing allows the apparatus to be used and perform its functions more unobtrusively, relative to prior art HME devices. The reduced dead space increase the use efficiency of heat and moisture passing into and/or generated in the housing.

The present apparatus preferably are of modular design. This reduces manufacturing costs and provides performance benefits which inure to the patient. For example, the housing has an inlet portion including the inlet and an outlet portion including the outlet. The inlet portion of the housing is detachably secured to the remainder of the housing and is adapted to be replaced, preferably together with the filter element, while the outlet portion of the housing remains connected to the tube(s) for passing respiratory gases. This detachable or separable inlet portion of the housing is very effective in providing for reduced resistance to flow of respiratory gases through the housing. For example, after a period of time, material such as mucous from the patient tends to collect and/or settle on the filter element, creating a flow resistance. Rather than having to replace the entire apparatus, the inlet portion of the housing is removed, together with the filter element. A new inlet portion/filter element combination is substituted and the resistance to respiratory gas flow is reduced.

The filter element preferably is secured to the inlet portion of the housing. In one very useful embodiment, the inlet portion of the housing includes a first portion of a dogging assembly and the outlet portion of the housing includes a second portion of the dogging assembly positioned to matingly engage the first portion to detachably secure the inlet portion to the outlet portion of the housing. The inlet portion of the housing preferably includes a peripheral ring or rim extending radially outwardly of the first portion of the dogging assembly. This peripheral rim is adapted to prevent the inlet portion of the housing from snagging other objects, for example, on the patient in the operating or treatment room. This feature allows for movement of the apparatus on or about the patient without the apparatus being snagged or otherwise caught up on such other objects. This feature advantageously reduces the risk of the tracheal tube connection to the patient being disturbed by such movement and, thus, reduces the risk of trauma to the patient.

In another useful embodiment, the outlet portion of the housing is rotatable relative to the inlet portion of the housing. For example, the housing may include an intermediate portion located between the inlet portion and the outlet portion of the housing. The outlet portion includes a first groove and the inlet portion includes a second groove positioned and adapted to matingly engage the first groove to rotatably secure the outlet portion to the intermediate portion. This rotation or swiveling between the various components of the housing allows for movement of the apparatus or reorientation of the apparatus with reduced risk of disturbing the tracheal tube in the patient by such movement.

A very useful embodiment provides that the housing includes a first intermediate portion, and that a generating material is located in this first intermediate portion. This generating material is adapted to generate water available to humidify gases passing through the housing. The first intermediate portion of the housing is detachably secured to the outlet portion of the housing. Further, the apparatus preferably includes an additional amount of generating material located in the housing adjacent the generating material noted above. This additional amount of generating material is adapted to be replaced while the first intermediate portion is detached from the outlet portion and the outlet portion remains connected to the tube(s) for passing respiratory gases. By replacing the additional amount of generating material, the effective useful life of the apparatus can be extended.

In one embodiment, the present apparatus preferably includes a fitting joined to both the housing and the tracheal tube device. The fitting defines a gas flow path which is substantially perpendicular to the flow path of respiratory gases passing through the housing.

In another useful feature of the present apparatus the inlet is rotatable relative to the remainder of the housing. For example, the inlet includes an open end away from the tracheal tube device having an outwardly extending annular flange. The housing includes an upwardly extending annular projection located in proximity to the outermost end of the flange. A ring member, preferably secured to the housing, is positioned so as to capture the projection and prevent the flange from separating from the housing. In addition, the ring receives the annular flange so that the annular flange is rotatable relative to the remainder of the housing. A fitting is preferably joined to both the inlet and the tracheal tube device and has a gas flow path which passes through an angle of about 90°, for example, is an elbow-like fitting.

In yet another broad aspect of the present invention, the apparatus comprise a housing, generally as described herein, a baffle assembly, and a gas permeable member, generally as described herein. The housing includes an inlet which defines an inlet passage. The baffle assembly is positioned so as to be effective in reducing the kinetic energy of mucous passing from the tracheal tube device. Reducing the kinetic energy of such mucous causes the mucous to collect relatively closer to the periphery of a housing member, thereby prolonging the useful life of the present apparatus. The baffle assembly preferably includes two spaced apart sets of baffles extending from the housing to the inlet passage. A fitting preferably is included and is joined to both the housing and the tracheal tube device and the baffle assembly is located in the fitting. The fitting preferably defines a gas flow path which is substantially perpendicular to the flow path of the respiratory gases through the housing. The baffle assembly, in one embodiment, includes two spaced apart sets of baffles extending inwardly from the fitting into this gas flow path.

In a very useful embodiment, the spaced apart sets of baffles define a guide path through the fitting sized to allow an elongated member, such as a catheter and the like, to be passed therein in treating the patient, for example, in removing mucous from a patient, through the tracheal tube device. The fitting includes one opening connected to the tracheal tube device and may include a second opening, preferably a substantially opposing second opening, through which respiratory gases can be sampled. A filter element, as described herein, preferably is included and is located in the housing.

The housing preferably includes a through port through which mucous from the tracheal tube device having passed across the baffle assembly is removed from the housing. This approach is particularly effective because the baffle assembly has reduced the kinetic energy of the mucous causing it to collect or pool near the periphery of the housing. The port, which is located to have access to the inner periphery of the housing, is effective in removing such mucous, for example, using a conventional suctioning device. Removing such mucous results in advantageously increasing the effective useful life of the apparatus.

In a further aspect of the invention, the apparatus comprise a housing, as described herein, a gas permeable membrane, as described herein, and an amount of generating material, as described herein. The generating material, such as a carbon dioxide absorbing material and the like, is positioned in the housing so as to prolong the effectiveness of, that is to extend the effective useful life of, the generating material to generate water relative to an identical amount of the same generating material positioned as a layer of uniform thickness across substantially the entire flow path of respiratory gases passing through the housing from the inlet to the outlet.

One advantage of such an apparatus is to allow useful humidification enhancement to the respiratory gases over a relatively long period of time, for example, during long surgical procedures. The present apparatus, in effect, makes more efficient or effective use of the generating material by positioning the generating material in the housing as other than a layer of uniform thickness across substantially the entire flow path of the respiratory gases passing through the housing from the inlet to the outlet. For example, in one embodiment, the generating material is positioned as a layer of non-uniform thickness across substantially the entire flow path of the respiratory gases passing through the housing from the inlet to the outlet. Thus, for example, the layer of generating material may include a peripheral region having a first thickness and a central region having a second thickness which is greater than the first thickness.

In a particularly useful embodiment, a valve assembly is provided in the housing and is adapted to cause a portion of the respiratory gases passing through the housing from the inlet (adapted for connection to a tracheal tube device) to the outlet (adapted for connection to the tube or tubes for passing respiratory gases) to bypass the generating material. Such bypass effectively extends the useful life of the generating material in the present apparatus. The valve assembly preferably is further adapted to cause all the respiratory gases passing through the housing from the outlet to the inlet to contact the generating material. Thus, gases which are exhaled from the patient partially bypass the generating material, whereas gases which are inhaled by the patient are routed so that all such gases contact the generating material. This provides an effective use of the generating material while, at the same time, minimizing the amount of moisture which is lost, for example, is condensed or otherwise passed outside the housing, and unavailable to the patient.

Yet a further aspect of the present invention is directed to apparatus which comprise a housing having an inlet portion and an outlet portion, as described herein, a filter element, as described herein, a gas permeable member, as described herein, and a humidification member. The humidification member is separate from the filter element and the gas permeable member and is located in the housing. This humidification member is adapted to receive moisture supplied from outside the housing and to transfer the moisture to respiratory gases passing through the housing.

The housing preferably includes a port through which moisture is supplied to the humidification member. The humidification member preferably is located closer to the outlet then the filter element and/or the gas permeable member. Although any useful material can be employed as the humidification member. It is preferred that it be a hydrophilic polymeric material or, more preferably, a hydrophilic open cell foam material.

In another broad aspect of the present invention, the apparatus comprise a housing, as described herein, a gas permeable member, as described herein, a generating material, as described herein, and a hygroscopic component positioned in the housing separate and apart from the gas permeable and the generating material. The hygroscopic material, such as calcium chloride and the like, is adapted to generate heat available to heat respiratory gases passing through the housing. The use of a separate hygroscopic component effectively provides a very quick heat input to the respiratory gases being passed to the patient without adversely interfering with the operation of the other components in the housing. Such a hygroscopic component very effectively reduces trauma and increases patient comfort, particularly during the start-up of the present apparatus.

Preferably, the hygroscopic component is positioned between the outlet and the gas permeable member, and the generating material is positioned between the inlet and the gas permeable member. This arrangement of materials within the housing very effectively uses moisture which might otherwise be lost down the exhaled gas tubing (and, thus, unavailable to the patient) to interact with the hygroscopic component produce heat to warm respiratory gases which are passed to the patient. Thus, moisture which may condense or otherwise be lost to the patient is, in effect, converted to very useful and welcomed heat which warms respiratory gases passed to the patient, for example, on the next inhalation breath. The patient is provided with this heat benefit from moisture which would otherwise be lost to the patient.

One additional broad aspect of the invention is directed to apparatus which include a housing, as described herein, a gas permeable member, as described herein, and a cover member secured to the housing and effective to reduce heat loss from the housing. In a very useful embodiment, the cover member includes a heat generating material effective to provide heat to the housing, and ultimately to the respiratory gases passing through the housing. The heat generating material preferably is effective to generate heat in response to being exposed to oxygen.

In one useful configuration, the cover member further includes a cover shell positioned so that the heat generating material is located between the cover shell and the housing. This is very effective in maintaining the heat generating material in place and, at the same time, preferably acts to direct the heat generated toward the housing. The cover shell preferably is structured to allow the heat generating material to be exposed to oxygen.

One further broad aspect of the invention provides apparatus which comprise a housing, as described herein, a gas permeable member, as described herein, and an amount of heat generating material located in the housing between the inlet and the outlet and adapted to generate heat available to warm respiratory gases passing through the housing. The heat generating material is effective to generate heat independent of water generation and water present in respiratory gases passing through the housing. Preferably, the heat generating material in the housing is effective to generate heat in response to oxygen present in respiratory gases passing through the housing.

In one embodiment, the heat generating material in the housing is positioned separate and apart from the gas permeable member. Alternately, the heat generating material can be located within or combined with the gas permeable member. The heat generating material preferably is provided so as to control the amount and rate of heat generation from the heat generating material. For example, the heat generating material may be coated with a hydrophobic, oxygen permeable substance effective to reduce the deleterious effect of the water in the housing on the heat generating material. In other words, the heat generating material preferably is configured so that the other components within the housing have a reduced, or even substantially minimal, effect on heat generation.

In one embodiment, the apparatus further comprises a water, preferably liquid water, delivery assembly containing water and located in the housing. The water delivery assembly is adapted to provide water to respiratory gases passing through the housing over time. The water delivery assembly may include a liquid water reservoir and a hollow tubular member including a first end in fluid communication with the liquid water reservoir and an opposing open second end exposed to respiratory gases passing through the housing. The liquid water reservoir preferably is adapted to be refillable while the housing is connected to the tracheal tube device.

Each individual feature and each combination of two or more features described herein are included within the scope of the present invention provided that the features included in the combination are not mutually inconsistent.

Commonly assigned U.S. patent application Ser. No. 09/113,649 filed on Jul. 10, 1998 herewith discloses additional features which can be used in combination with the present apparatus. The disclosure of this application, in its entirety, is incorporated by reference herein.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 4 is a front view, partly in cross section, of the embodiment of the apparatus shown in FIG. 1.

FIG. 5 is a front view, in cross section, of another embodiment of an apparatus in accordance with the present invention.

FIG. 9 is a partial view, partly in cross section, of an alternate embodiment of apparatus in accordance with the present invention.

FIG. 10 is a front view, partly in cross section, of a further embodiment of the present apparatus.

FIG. 11 is a cross sectional, detailed view of the port structure of the apparatus shown in FIG. 9.

FIG. 12 is a front side view, in perspective, of an additional embodiment of an apparatus in accordance with the present invention.

FIG. 13 is a front view, partly in cross section, of the apparatus shown in FIG. 12.

FIG. 13A is a fragmentary view of an alternate generating material useful in the apparatus shown in FIG. 12.

FIG. 14 is a cross sectional view taken generally along arc 14 of FIG. 13.

DETAILED DESCRIPTION OF THE DRAWINGS

Figure 1:
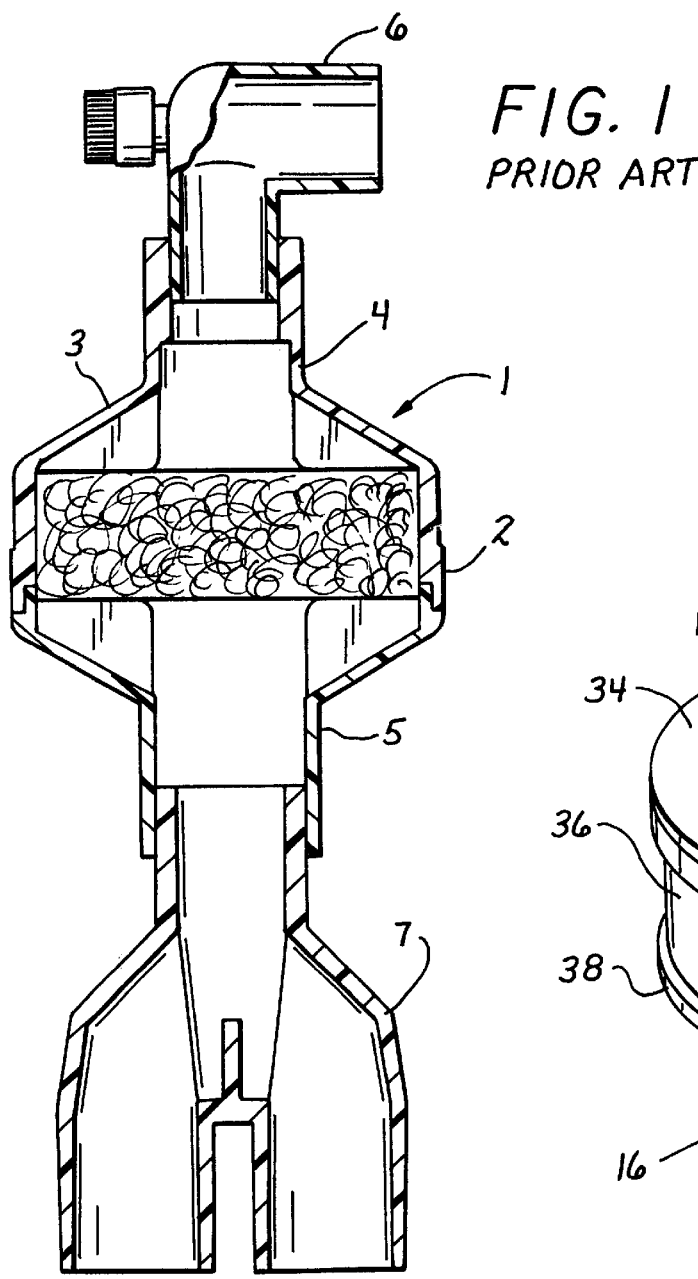
FIG. 1 is a front side view, partly in cross section of a prior art device used to exchange heat and moisture with respiratory gases.

With reference to FIG. 1, an example of a commercially available HME unit, shown generally at 1, includes a heat and moisture exchange (HME) member 2 enclosed in a housing 3 including an inlet 4 and an outlet 5. An elbow fitting 6 is connected to the inlet 4 of the housing 3. This elbow fitting 6 is adapted to be connected to a tracheal tube device, not shown.

A manifold 7, adapted to be connected to a device for passing respiratory gases, is connected to the outlet 5 of housing 3.

One important disadvantage of the prior art device 1 is the substantial amounts of open or dead space located both above and below the HME member 2. Such space is detrimental for a number of reasons. For example, this dead space allows for heat transfer to the environment surrounding the HME unit 1, which reduces the heat transfer effectiveness to the respiratory gases passing into the patient in whom the tracheal tube device is located. Moisture condensation can also result, thereby reducing the amount of humidification in the respiratory gases being passed to the patient. Further, the size or bulkiness of the HME unit 1 may make it difficult to handle during use and may also be a physical impediment or obstacle during the surgery or other treatment of the patient.

Figure 2:
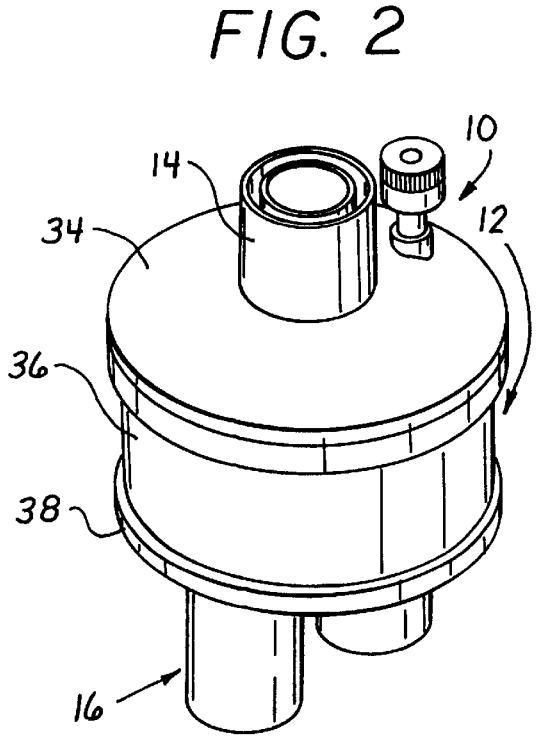
FIG. 2 is a front side view, in perspective, of one embodiment of the present apparatus for heat and moisture exchange with respiratory gases.
Figure 3:
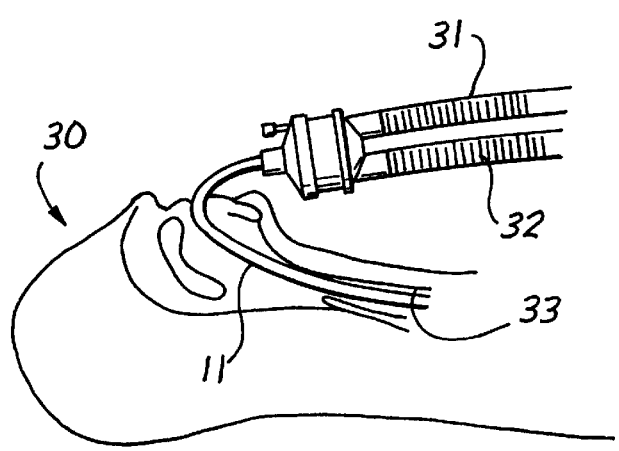
FIG. 3 is a schematic illustration showing the embodiment of the present invention shown in FIG. 1 being used for heat and moisture exchange with respect to respiratory gases passed to and from a patient.

An embodiment of the apparatus in accordance with the present invention is shown in FIGS. 2, 3 and 4. This apparatus, shown generally at 10, includes a housing 12 having an inlet 14 and a two tube outlet 16. With particular reference to FIG. 4, apparatus 10 includes a filter element 18, generating material 20 and a gas permeable member 22.

FIG. 3 shows a patient 30 being treated so as to provide respiratory gases to the patient. A tracheal tube 12 is connected to the inlet 14 of the apparatus 10. The outlet 16 of the apparatus 10 is joined or connected to two tubes 31 and 32 with communicate with an anesthesia machine or a ventilator (not shown). In this arrangement, the patient 30 is provided with respiratory gases from the anesthesia machine or ventilator through inspiratory tube 32. Such gases pass into the apparatus 10, and through tracheal tube 11 into the trachea 33 of patient 30. Exhaled respiratory gases passed from the trachea 33 through the tracheal tube 12 and the apparatus 20 and into the expiratory tube 31. This cycle is repeated each time patient 30 inhales and exhales respiratory gases.

As shown in FIGS. 2 and 4, housing 12 includes a first housing section 34, a second housing section 36 and a third housing section 38. Housing 12 can be made of any suitable material of construction. Preferably, housing 12 is made of polymeric material. First, second and third housing sections 34, 36 and 38 are joined together as is discussed hereinafter with regard to the apparatus shown in FIG. 5. First, second and third housing sections 34, 36 and 38 are structured so as to minimize the amount of open or dead space above filter element 18 and below gas permeable member 22. This provides for more efficient and effective heat and moisture transfer, for example, relative to commercially available HME unit 1. In addition, the size of apparatus 10 is small relative to the size of HME unit 1. This provides for relative ease in using the apparatus 10 and reduces the amount of space taken up by the apparatus.

First, second and third housing sections 34, 36 and 38 can be bonded together to provide for total disposability, for example, when the apparatus is to be used a relatively short period of time. When housing sections 34, 36 and 38 are joined together, a hollow chamber 39 is formed by this coupled structured. Located within the chamber 39 and extending substantially across the entire cross-section of the chamber are the antimicrobial filter element 18 which is secured to the first housing section 34, a quantity of particulate generating material 20, in particular, particulate carbon dioxide absorbing material, and a gas permeable member 22, in particular a fibrous member.

Respiratory gases from patient 30 pass through inlet passage 40 defined by inlet 14 and into chamber 39. Inlet 14 is part of first housing section 34. Such respiratory gases pass through filter element 18, generating material 20 and gas permeable member 22 before exiting through outlet passage 42 defined by outlet 16. Outlet 16 is part of third housing section 38. When respiratory gases are to be inhaled by patient 30, such gases pass into apparatus 10 through outlet passage 42 into chamber 39, across gas permeable member 22, generating material 20 and filter element 18. This respiratory gas to be inhaled is passed through inlet passage 40 into tracheal tube 11 and into the trachea 33 of the patient 30.

The filter element 18, generating material 22 and gas permeable member 22 are all positioned substantially perpendicular to the longitudinal axis 45 of apparatus 10. Thus, the filter element 18, generating material 20 and gas permeable member 22 are all substantially perpendicular to the general direction of flow between the inlet passage 40 and the outlet passage 42.

The filter element 18 may be of any suitable configuration to remove contaminants from the respiratory gas passing therethrough. The filter element 18 should be sufficiently gas permeable so that the respiratory gases passing therethrough result in a relatively reduced, or even minimal pressure differential. The filter element 18 may be chosen from filter material used in conventional respiratory filters or heat and moisture exchangers for respiratory gases, many of which are known and commercially available. The filter element 18 may have antimicrobial activity.

The gas permeable member 22 is selected to provide for both heat and moisture exchange with gases passing through the housing 12. The gas permeable member may be chosen from any suitable material which is effective as a heat and moisture exchanging material and has gas permeability. Examples of useful materials from which gas permeable member 22 can be chosen include such materials which are conventionally used in heat and moisture exchangers for respiratory gases, many of which are well known and commercially available.

The generating material 20, which is located between and adjacent the filter element 18 and the gas permeable member 22, is effective to generate both water and heat, preferably in response to an interaction with carbon dioxide, for example, absorption of and subsequent reaction with carbon dioxide, in the respiratory gas which comes in contact with the generating material. The carbon dioxide generating material making up generating material 22 preferably is in the form of particles which are effective to absorb, or otherwise interact with, carbon dioxide in the respiratory gases. The generating material 20 preferably is sufficiently gas permeable so that respiratory gases passing therethrough result in a substantially reduced, or even in a minimal pressure differential.

Without wishing to limit the invention to any particular theory of operation, it is believed that the generating material is effective to neutralize carbon dioxide with resultant production of heat and water. Using one particularly useful carbon dioxide absorbing generating material, such neutralization is believed to proceed as follows:

$$CO_2 + H_2O \rightleftharpoons H_2CO_3 \qquad (I)$$

$$2H_2CO_3 + 2NA^+ + 2OH^- + 2K + 2OH^{31} \rightleftharpoons 2NA^+ + CO_3 + 2K^+ + CO_3 + 4H_2O \qquad (ii)$$

$$CA(OH)_2 + H_2O \rightleftharpoons CA^{++} + 2OH^- + H_2O \qquad (iii)$$

$$2CA^{++} + 2OH^- + 2NA^+ + CO_3 + 2K^+ + CO_3 \rightleftharpoons 2CACO_3 + 2NA^+ + 2OH^- + 2K^+ + 2OH^- \qquad (iv)$$

In (I) the $CO_2$ dissolves at a rate governed by a number of physical chemical factors. The rate is not proportional to the partial pressure of the $CO_2$ which is in contact with the film of moisture coating the soda lime granules, but greater—because some of the $CO_2$ combines chemically with the water to form carbonic acid. The rate is directly proportional to the rate of removal of dissolved $CO_2$, or carbonic acid, from solution, by reaction with hydroxyl ion (reaction ii). Thus, the rapidity of removal of dissolved $CO_2$ is directly related to the availability of hydroxy ions. Since the reaction between H+ and OH– is instantaneous, forming water, reaction (iii) and (iv) must supply additional hydroxyl ions to keep the absorption of $CO_2$ progressing. The latter two reactions are therefore rate limiting.

In a very useful embodiment, the amount of generating material present is effective to generate only a portion, more preferably a minor portion (that is, no more than about 50%), of the water to humidify respiratory gases passing through the housing. In particular, the amount of generating material present in the housing is effective to generate at least about 50%, more preferably at least about 10%, and still more preferably at least about 15% of the water to humidify respiratory gases passing through the housing. On the other hand, the amount of generating material present in the housing preferably is effective to generate no more than about 50% of the moisture of the water to humidify respiratory gases passing through the housing. Having excessively large amounts generating material present in the housing can result in the respiratory gases passing to the patient having a temperature which is excessively high relative to the requirements of the patient. Therefore, it is preferred that only relatively reduced amounts of water and heat, as described herein, be generated by the generating material. In the event carbon dioxide absorbing material is used as the generating material, the present apparatus preferably initially includes about 10 or about 20 grams to about 40 or about 60 or about 80 grams, more preferably about 20 grams to about 30 or about 40 grams of such material, particularly when the patient in question is an adult human being. The amount of generating material used when the patient is a human infant or a premature human infant may be somewhat less because of the very small lung tidal volumes, for example, about 10 cc or less, involved.

This controlled or limited amount of water and heat generation makes it important to provide not only the generating material but also the gas permeable member, e.g., a conventional HME member, which acts in combination with the generating material to provide the desired, preferably controlled and acceptable, degree of humidification and heating to the respiratory gases being passed to the patient.

Because the generating material preferably interacts with carbon dioxide in the respiratory gases to generate the water, and preferably heat, the amount of carbon dioxide being exhaled by the patient provides a suitable control as to the amount of water, and preferably heat, generated by the generating material. Thus, increased respiration by the patient, which results in increased production of carbon dioxide, leads to increased water, and preferably heat, generation, which is useful in humidifying and heating the increased amounts of respiratory gases required by the patient. With the generating material generating water, and preferably heat, because of an interaction with carbon dioxide, the patient and his/her respiratory needs, in effect, control the amount of water, and preferably heat, being generated in the present apparatus.

The generating material preferably is positioned in the housing adjacent the gas permeable member. In a very useful embodiment, the generating material is located nearer to the inlet than is the gas permeable member. Thus, exhaled gases from the patient preferably come in contact with the generating material before being passed to the gas permeable membrane. This arrangement is effective to provide that at least a portion of the water and heat generated by the generating material is accumulated or collected by the gas permeable member and is available for use in humidifying and heating the respiratory gases being passed to the patient.

The generating material in the housing is often of such a character that after a period of time in service (in the present apparatus) a deactivated material is formed. For example, the generating material may include one or more active components which are consumed and/or otherwise rendered ineffective to generate water, and preferably heat, after time in service in the present apparatus. The deactivated material is derived from the generating material and preferably includes such consumed and/or otherwise ineffective components. In any event, the deactivated material has substantially no ability to generate water or heat available to humidify or heat respiratory gases passing through the housing. However, it has been found that the present apparatus including the deactivated material in place of the generating material has a greater ability to humidify and heat respiratory gases passing through the housing relative to an identical apparatus without either the generating material or the deactivated material.

Without wishing to limit the invention to any particular theory of operation, it is believed that the deactivated material, even though it is ineffective to generate water and heat, is at least to some extent effective to transfer, e.g., store or collect and release, moisture and heat with the respiratory gases passing through the housing. The apparatus with the deactivated material in place of the generating material has increased moisture/heat transfer capacity relative to an identical apparatus without either the generating material or the deactivated material. The present apparatus provide substantial benefits even though the generating material is rendered ineffective and forms the deactivated material.

Although any suitable component or combinations of components may be useful in generating material 20 to generate moisture and heat, it is preferred that the generating material be that sold by W. R. Grace under the trademark "SODA SORB".

The apparatus 10 functions as follows. The apparatus 10 is connected to the respiratory assist system of patient 30 as described above. As the patient exhales respiratory gases, such gases pass through inlet passage 40 into chamber 39. These exhaled gases pass through filter element 18 and are at least to some extent purified in that contaminants are removed and/or destroyed. This exhaled respiratory gas includes carbon dioxide at least a portion of which interacts with the generating material 20 as the exhaled respiratory gases pass therethrough. This results in the generation of heat and moisture which passes into gas permeable member 22, along with the heat and moisture originally present in the respiratory gases being exhaled by patient 30. This heat and moisture is collected by gas permeable member 22 as the exhaled respiratory gases pass therethrough. The exhaled respiratory gases pass out of apparatus 10 through outlet passage 42. During the time patient 30 is inhaling gases, respiratory gases to be inhaled are passed into apparatus 10 through outlet passage 42. The to be inhaled gases pass through the gas permeable member 22 where heat and moisture from the fibrous member are transferred to the respiratory gases to be inhaled. Additional heat and moisture is released to the respiratory gases to be inhaled as the gases pass through the generating material 20 to provide the desired amount of heat and moisture to such gases. Finally, the respiratory gases to be inhaled pass through the filter element 18 and out of apparatus 10 through inlet passage 40 into the tracheal tube 11 and trachea 33 of the patient 30.

This exhale/inhale cycle is continued with the result that the patient 30 is provided with respiratory gases which have the desired degree of heat and humidity so that the patient is not detrimentally affected by respiratory gases which are too dry or too cold.

The amount of generating material 20 is sufficient to provide about 20 percent to about 40 percent, more preferably about 25 percent, of the moisture to the respiratory gases to be inhaled by patient 30. Providing more than about 50 percent of the moisture to the respiratory gases to be inhaled can result in an excessive increase in the temperature of the inhaled gases which can have a detrimental effect on the patient 30.

Thus, it is important that both the generating material 20 and the gas permeable member 22 be used together, more preferably with the generating material on the inlet side of the gas permeable member, to provide a portion, for example, a minor portion, of the moisture, and preferably heat, to the respiratory gases inhaled by patient 30.

Over a period of time, the active component in generating material 20 is consumed. After a substantial amount of this component has been consumed, the apparatus 10 can be replaced by a new apparatus 10 simply by removing the used apparatus 10 and providing in its place a new apparatus 10 with a new generating material 20.

FIGS. 5 to 8 illustrate another embodiment of the present apparatus. Except as expressly described herein, this embodiment, shown generally at 210, is structured and functions similarly to apparatus 10. Components of apparatus 210 which correspond to components of apparatus 10 are identified by the same reference numeral increased by 200.

The primary differences between apparatus 210 and apparatus 10 involve the use of a modified inlet and a fitting, the inclusion of a fourth housing section and the use of two separate quantities of generating material.

Specifically, the inlet 214 of apparatus 210 is configured so that gases entering or leaving the inlet passage flow 240 in a general direction perpendicular to, that is, at an angle of about 90° to, the general flow of respiratory gases through the housing 212. The inlet 214 is configured to receive a fitting 48 which is adapted to be secured to both the inlet 214 of apparatus 210 and the tracheal tube device, in particular, at or near first end 50. The general direction of gas flow within fitting 48 is perpendicular to the general direction of flow of respiratory gases through housing 212. Fitting 48 includes a through port 52 which is adapted to allow respiratory gases from inlet passage 240 to pass into fitting 48. The outer surface 54 of fitting 48 includes an indexing notch 56 which is adapted to engage the inlet 214 so as to insure that the through port 52 provides fluid communication between the inlet passage 240 and the interior 58 of fitting 48.

The second end 60 of fitting 48 is normally closed, for example, by a cap (not shown). Thus, the respiratory gases passes between inlet passage 240 and the tracheal tube device (not shown) connected at or near first end 50 of fitting 48.

Figure 6:
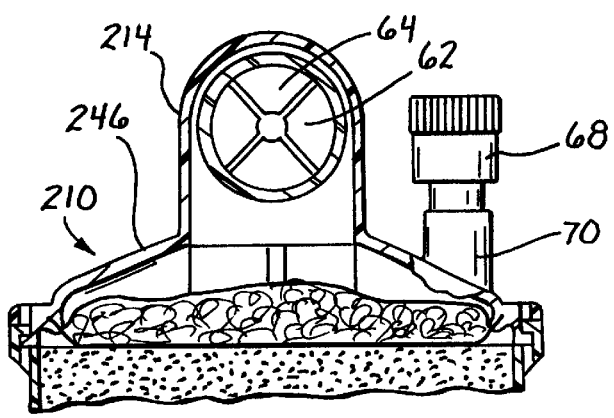
FIG. 6 is a view, partly in cross section, taken generally along line 6—6 of FIG. 5.
Figure 8:
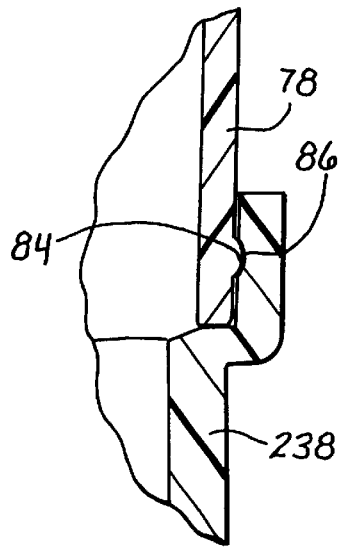
FIG. 8 is a view taken generally along arc 8 of FIG. 5.

Located within fitting 48 between through port 52 and first end 50 are two sets of baffles 62 and 64. These baffles extend inwardly from the inner sidewall 66 of fitting 48. Baffles 62 and 64 are positioned and configured to reduce the kinetic energy of mucous from the patient which passes through space 58 into inlet passage 240 and onto the top of filter element 218. By reducing the kinetic energy of the mucous passing into housing 212, the mucous tends to pool or collect near the periphery of the filter element 218. As seen in FIG. 6, a port 70 is provided on the top of first housing segment 234. By removing the cap 68 from the port 70, a conventional suctioning device can be inserted through the port to remove this pooled or collected mucous. By removing such mucous, the effective useful life of the filter element 218 and, in general, the apparatus 210, is increased. Thus, baffles 62 and 64 are very effective in providing a useful function.

In addition, baffles 62 and 64 are oriented to provide central openings 72 and 74, respectively. These central openings 72 and 74 provide a very effective guide path. Thus, a catheter or other elongated treatment instrument can be passed through the second opening 60 of fitting 48 through the openings 72 and 74 into the tracheal tube device to provide a further treatment to the patient 30. Openings 72 and 74 very effectively guide the catheter or other instrument to reduce the risk of causing trauma to the patient 30.

Housing 212 is modular in design. Thus, first housing section 234 is detachably secured to a fourth housing section 76 which is detachably secured to a second housing portion 78 which is rotatable about or relative to third housing section 238.

Figure 7:
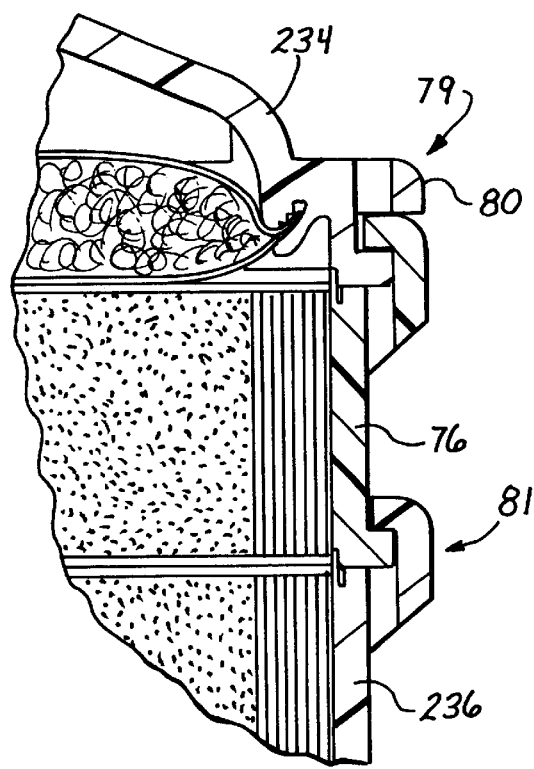
FIG. 7 is a view taken generally along arc 7 of FIG. 5.

With specific reference to FIG. 7, first housing section 234 is detachable from fourth housing section 76 using a dogging assembly 79.

The dogging assembly 79 is arranged and configured so that a peripheral rim surface 80 of first housing section 234 is provided. This peripheral rim 80 is rounded and continuous around the entire periphery of first housing section 234. This rounded peripheral rim is very effective in reducing the risk that the apparatus 210 will snag or otherwise be caught up on the patient, his/her garments and/or other objects used in treating the patient. In turn, this reduces the risk of causing trauma to the patient as a result of the tracheal tube being jousted about because of such snagging, etc.

Again, with reference to FIG. 7, second housing section 236 is detachably secured to fourth housing section 76 using a substantially similar dogging assembly 81.

Having first housing section 234 detachable from first fourth housing section 76 very conveniently allows the first housing section to be removed from apparatus 210, as desired. For example, if filter element 218 becomes contaminated with mucous and/or otherwise results in an unacceptably high pressure differential, the filter element and first housing section 234 can be removed as a unit and replaced by a similar new component. In addition, being able to remove first housing section 234 from fourth intermediate housing section 76, allows the operator to remove the upper layer 81 of the generating material. Thus, by replacing the consumed generating material layer 81 with a new generating material layer, the overall effectiveness of apparatus 210 is increased, in particular the effective useful life of apparatus 210 is increased. Similarly, by being able to detach the fourth housing section 76 from the second housing section 236, both layer 81 and second layer 82 of generating material can be removed and replaced, thereby even further extending the effective useful life of apparatus 210.

An additional feature of apparatus 110 has to do with second housing section 236 being rotatable relative to third housing section 238. This is accomplished as shown with reference to FIG. 8. Thus, second housing section 236 includes a peripheral groove 84, in the form of a outwardly extending projection. Third housing section 238 includes an annular recess 86 which also extends around the entire periphery of housing 212 and is adapted to matingly engage the projection 84. This combination of projection 84 and recess 86 allows second housing section 236 to rotate about third housing section 238. This is very effective in allowing the orientation of apparatus 210 and fitting 48 to be flexible so as to reduce the risk of causing trauma to the patient as a result of the movement of apparatus 210 and/or third housing section 238.

FIG. 9 illustrates another embodiment of the present apparatus. Except as expressly described herein, this embodiment, shown generally at 10, is structured and functions similarly to apparatus 210. Components of apparatus 310 which correspond to components of apparatus 210 are identified by the same reference numeral increased by 100.

The primary differences between apparatus 310 and apparatus 210 involve the structure of the inlet 314 and the configuration of the generating material.

Specifically, apparatus 310 includes an elongated inlet 314 which is joined to an elbow-type fitting 84. Elbow-type fitting 84 is also connected to the tracheal tube device (not shown). Two sets of baffles 86 and 88 extend from the inner side wall 90 of inlet 314 into the inlet passage 340. These baffles 86 and 88 are positioned and configured to reduce the kinetic energy of mucous from the patient which passes through inlet passage 340 and onto the top of filter element 318. By reducing the kinetic energy of the mucous passing into housing 312, the mucous tends to pool or collect near the periphery of the filter element 318. Port 170 is located on the top of first housing segment 334. By removing the cap 168 from the port 170, a conventional suctioning device can be inserted through the port to remove this pooled or collected mucous.

Fourth housing section 176 includes a layer of generating material 96, as described herein, surrounding a valve assembly, shown generally at 94. Valve assembly 94 includes a plurality of valve leafs 96 which are movable between a closed position in which no respiratory gas is allowed to flow across the valve assembly and an open position in which respiratory gases are allowed to flow across the valve assembly. A valve seat 98 is provided on which valve leafs 96 are positioned when the valve assembly 94 is in the closed position.

The operation of valve assembly 94 is illustrated as follows. As the patient exhales, respiratory gases pass through the filter element 318. These respiratory gases cause valve assembly 94 to open which allows a substantial portion of the exhaled gases to flow through space 100 and toward the outlet of apparatus 310. As the patient inhales, respiratory gases flow from the outlet of apparatus 310 and cause the valve assembly 94 to close. This causes substantially all of the inhaled gases to pass through the layer of generating material 92. In summary, as gases are exhaled from the patient the layer of generating material 92 is at least partially bypassed, whereas as the patient inhales substantially all of the inhaled gas passes through the layer of generating material. This partial bypass of the layer of generating material 92, in effect, increases the effective useful life of the generating material so that the apparatus 310 requires replacement less frequently or can be used for longer periods of time. It should be noted that apparatus 310 need not include a second layer of generating material, such as layer 82 in apparatus 210.

FIG. 10 illustrates a further embodiment of the present apparatus. Except as expressly described herein, this embodiment, shown generally at 410, is structured and functions similarly to apparatus 210. Components of apparatus 410 which correspond to components of apparatus 210 are identified by the same reference numeral increased by 100.

The primary differences between apparatus 410 and apparatus 10 involve the configuration of the generating material and the elimination of the fourth housing section. In addition, no baffles are shown in FIG. 10, although a baffle configuration, for example, as illustrated in FIG. 5, can be employed.

Specifically, first housing section 434 is detachably secured to second housing section 436. The second housing section 436 of housing 412 includes a quantity of generating material 102 which is in the form of a non-uniform layer. In particular, generating material 102 includes a peripheral region 103 having a first depth, parallel to the longitudinal axis of apparatus 410, and a central region 106 having a second depth which is larger than the first depth. The gas permeable member 108 surrounds the central region 106.

The configuration of generating material 102, as shown in FIG. 10, effectively prolongs the usefulness of the generating material to produce both heat and moisture for use in heating and humidifying respiratory gases passed to the patient. Thus, the generating material 102, as shown in FIG. 10, provides for a longer period of heat and moisture generation relative to a similar apparatus using the same quantity of an identical generating material located in a substantially constant depth layer.

FIGS. 12 to 14 illustrate an additional embodiment of the present apparatus. Except as expressly described herein, this embodiment, shown generally at 510, is structured and functions similarly to apparatus 10. Components of apparatus 510 which correspond to components of apparatus 10 are identified by the same reference numeral increased by 500.

The primary differences between apparatus 510 and apparatus 10 involve the use of a rotatable inlet, and the general shape of the housing.

Specifically, the housing 512 of apparatus 510 has an oval or elliptical cross-section rather than the circular configuration of housing 12 of apparatus 10. This oval or elliptical cross-section of housing 512 allows the apparatus 510 to have more stability, for example, in being positioned with respect to, for example, on the chest of, the patient being treated.

In addition, the inlet 514 of apparatus 510 is constructed as a separate part, that is, is separate from the first housing section 534 of apparatus 510. As shown in FIG. 14, inlet 514 includes an outwardly extending annular flange 111. The first housing section 534 includes an upwardly extending annular projection 113. A cover element 115 is sized and adapted to receive the projection 113 and to extend inwardly toward the inlet 114. The end 117 of cover element 114 is adapted to entrap a portion of the flange 111 in such a way that inlet 514 can be rotated about first housing section 534. The ability to rotate inlet 514 relative to the housing 512 allows for a substantial amount of flexibility in orienting the housing and/or the tracheal tube device so as to effectively reduce the risk of trauma to the patient caused by movement of apparatus 510 or any of its component parts.

Although it is not shown in FIGS. 12 to 14, the rotatable inlet can be employed together with rotating the second housing section relative to the third housing section, for example, as shown in FIGS. 5 to 8.

With regard to FIG. 13A, the generating material 520, can be combined with particles of a heat generating material 119 which are coated with a hydrophobic oxygen permeable material 121. The particles of heat generating material can be, for example, particles of iron and/or other metal or metals, active carbon and the like, which are effective, when exposed to oxygen, to generate heat. The hydrophobic oxygen permeable coating for these particles can be, for example, a micro porous polymeric material, such as a polyflourohydrocarbon material and the like which can be treated to provide additional hydrophobicity. Such coatings reduce any deleterious effect or effects that water located in housing 512 may have on the heat generating material 119. The use of a heat generating material, such as 119, assists in providing the desired amount of heat to the respiratory gases being passed to the patient, which adds to the comfort of the patient.

Figure 16:
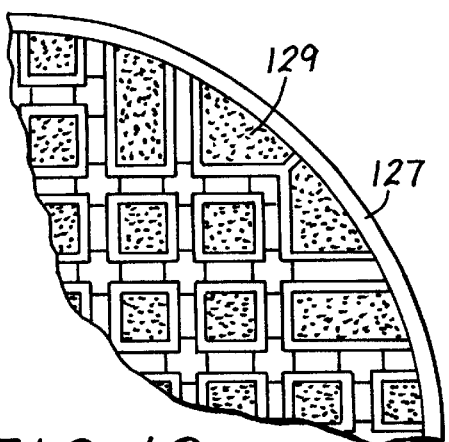
FIG. 16 is a partial top view of a tray-like member included in the apparatus shown in FIG. 15.
Figure 15:
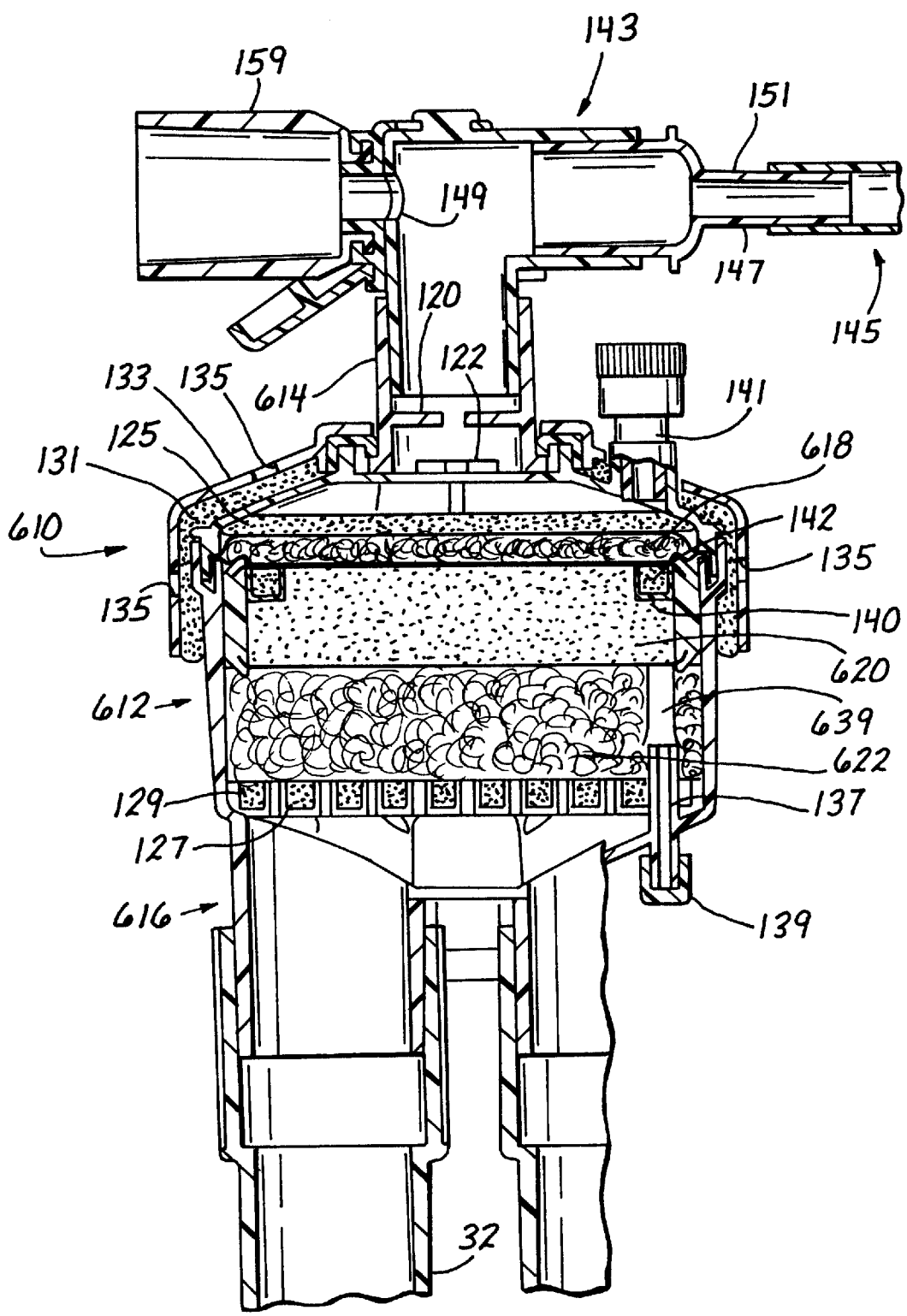
FIG. 15 is a front view, partly in cross section, of yet another embodiment of the apparatus in accordance with the present invention.

FIGS. 15 and 16 illustrate yet another embodiment of the present apparatus. Except as expressly described herein, this embodiment, shown generally at 610, is structured and functions similarly to apparatus 10. Components of apparatus 610 which correspond to components of apparatus 10 are identified by the same reference numeral increased by 600.

The primary differences between apparatus 610 and apparatus 10 involve the use of a modified inlet, a modified housing and a modified fitting. Also, additional materials are located in the housing to provide benefits for the patient.

Apparatus 610 includes an inlet 614 with a set of kinetic energy reducing baffles 120 and 122 similar in structure and functioning to baffles 86 and 88 of apparatus 310 shown in FIG. 9. In addition, inlet 614 is rotatable about housing 612 in a manner substantially similar to inlet 514 of apparatus 510 shown in FIGS. 12 to 14.

The housing 612 includes filter element 618, generating material 620 and gas permeable member 622. In addition, housing 612 includes a layer of hydrophilic open cell foam material 125 which is located between filter element 618 and inlet 614. Further, a tray-like element 127 including a quantity of hygroscopic material 129, for example, calcium chloride and the like, is located in housing 612 between gas permeable member 622 and outlet 616. The exterior of housing 612 includes a layer of heat generating material 131 similar in composition to heat generating material 119, described previously. Layer 131 substantially surrounds the upper or inlet portion of housing 612, and extends downwardly to approximately the level between the generating material 620 and gas permeable member 622. A heat reflective cover shell 133, for example, made of a polymer material having a heat reflective substance coated on the inner surface of the shell, is located on housing 612 so as to cover the heat generating material layer 131. Cover shell 133 includes through holes 135 located around the cover shell so as to provide access for oxygen to the heat generating material, thereby allowing heat to the generated from this material.

Housing 612 includes a hollow tubular construction 137 which extends from outside the chamber 639 defined by the housing to inside the chamber. A cap 139 covers the tubular construction 137. The cap 139 can be removed to provide water through tubular construction 137 to the chamber 639. The tubular construction 137 can be considered a reservoir for water to be used in housing 612, as well as a conduit to provide this water to the chamber 639. In addition, port 141 can be employed to add water directly to the hydrophilic foam layer 125. An annular ring 140 is situated near the top of generating material 620, and holds a buffering material 142, for example, a conventional pH buffer, which acts to modulate the pH (acidity/alkalinity) of liquid water condensed or otherwise present in the housing 612 toward a neutral pH of 7. The ring 140/buffering material 142 combination may be situated at other locations in the housing 612, for example, between the filter 618 and hydrophilic foam layer 125.

Because of the presence of the heat generating material 131, the apparatus 610 is shipped and stored in packaging which is not permeable to oxygen. Also, the apparatus 610 is, during shipment and storage, maintained substantially totally dry. Thus, when it is desired to use apparatus 610, it is removed from the packaging and secured to the tracheal tube device and the tubes for providing respiratory gases. In order to reduce the "start up" phase of the operation of apparatus 610, water is added to the hydrophilic foam material layer 125 through port 141. Removing the apparatus 610 from the packaging causes oxygen to contact the heating material in layer 131 which generates heat that is transferred inwardly into the chamber 639. Thereafter, the heat generating material layer 131 continues to provide heat to chamber 639, thereby assisting in heating the respiratory gases being passed to the patient. In addition, detrimental heat loss from chamber 639 through housing 612 is reduced.

The hygroscopic material 129 is very effective in assisting the apparatus 610 during initial or "start-up" operation of the apparatus. The hygroscopic material 129 comes in contact with water from respiratory gases passing through the housing 612 and produces heat which is available for transfer to the respiratory gases being passed to the patient. The location of the hygroscopic material 129 near the outlet 616 of housing 612 is beneficial in that moisture which interacts with the hygroscopic material to generate heat would, if not so interacted, be removed from the apparatus 610 and become unavailable to the patient. Placing the hygroscopic material 129 at this location, therefore, provides a substantial benefit to the patient from moisture which would otherwise be lost to the patient. The tray-like element 127, shown in detail in FIG. 16, is constructed so that respiratory gases passing out of the housing 612 contact the hygroscopic material 129 and interact to generate heat. As respiratory gases move into the housing 612 across tray-like element 127, such gases pick up the heat produced by the hygroscopic material 129 and provide warmed respiratory gases to the patient.

The present apparatus are directed to providing respiratory gases to a patient undergoing surgery or other treatment procedure. The apparatus effectively provide heat and moisture to such respiratory gases so as to reduce the risk of trauma to the patient and increase the patient's comfort and safety. Moreover, the present apparatus are very flexible in use, preferably being adapted to provide for additional amounts of heat and/or moisture for exchange with respiratory gases so as to effectively maintain the comfort and safety of the patient undergoing treatment.

While this invention has been described with respect to various specific examples and embodiments, it is to be understood that the invention is not limited thereto and that it can be variously practiced within the scope of the following claims.

What is claimed is:

1. An apparatus for heating and humidifying respiratory gases comprising:
    a housing having a first port adapted for connection to a tracheal tube device and a second port adapted for connection to a tube for passing respiratory gases to and from the housing, the first port and the second port being positioned so that respiratory gases passing to and from the housing pass therebetween;
    a gas permeable member positioned in the housing between the first port and the second port and having a size and structure suitable to exchange effective amounts of heat and moisture with respiratory gases passing to and from the housing; and
    a generating material located in the housing between the first port and the second port and being present in an amount effective to generate water available to humidify respiratory gases passing through the housing, the generating material being positioned in the housing as a layer of non-uniform thickness across substantially the entire flow path of respiratory gases passing through the housing from the first port to the second port, wherein the layer of non-uniform thickness includes a peripheral region having a first thickness, and a central region having a second thickness which is greater than the first thickness, so as to prolong the time the generating material is used to generate water available to humidify respiratory gases relative to an identical generating material present in a similar apparatus in an amount equal to the amount of the generating material and positioned as a layer of uniform thickness across substantially the entire flow path of respiratory gases passing through the housing from the second port.

2. The apparatus of claim 1 wherein the first port is connected to a tracheal tube device and the second port is connected to at tube for passing respiratory gases to and form the housing.

3. The apparatus of claim 11 wherein the generating material is present in the housing in an amount of less than about 80 grams.

4. The apparatus of claim 1 further comprising a hygroscopic component positioned in the housing and being adapted to generate heat available to heat respiratory gases passing through the housing.

5. An apparatus for heating and humidifying respiratory gases comprising:
    a housing having a first port adapted for connection to a tracheal tube device and a second port adapted for connection to a tube for passing respiratory gases to and from the housing, the first port and the second port being positioned so that respiratory gases passing to and from the housing pass therebetween;
    a gas permeable member positioned in the housing between the first port and the second port and having a size and structure suitable to exchange effective amounts of heat and moisture with respiratory gases passing to and from the housing;
    a generating material located in the housing between the first port and the second port and being present in an amount effective to generate water available to humidify respiratory gases passing through the housing, the generating material being positioned in the housing so as to prolong the time the generating material is used to generate water available to humidify respiratory gases relative to an identical generating material present in a similar apparatus in an amount equal to the amount of the generating material and positioned as a layer of uniform thickness across substantially the entire flow path of respiratory gases passing through the housing from the second port; and
    a valve assembly positioned in said housing and adapted to cause a portion of respiratory gases passing through the housing from the first port to the second port to bypass the generating material.

6. The apparatus of claim 5 wherein said valve assembly is further adapted to cause all respiratory gases passing through the housing from the second port to the first port to contact the generating material.

7. The apparatus of claim 5 wherein the first port is connected to a tracheal tube device and the second port is connected to a tube for passing respiratory gases to and from the housing.

8. The apparatus of claim 5 wherein the generating material is present in the housing in an amount of less than about 80 grams.

9. The apparatus of claim 5 further comprising a hygroscopic component positioned in the housing and being adapted to generate heat available to heat respiratory gases passing through the housing.

10. An apparatus for heating and humidifying respiratory gases comprising:

a housing having a first port connected to a tracheal tube device and a second port connected to a tube for passing respiratory gases to and from the housing, the first port and the second port being positioned to allow a bidirectional flow of respiratory gasses between the patient and the housing;

a gas permeable member positioned in the housing between the first port and the second port and having a size and structure effective to exchange heat and moisture between the respiratory gases passing to the housing and respiratory gases passing from the housing; and a generating material located in the housing between the first port and the second port and being present in an amount effective to generate water available to humidify the respiratory gasses passing through the housing, the generating material being positioned as a layer of non-uniform thickness in the housing so as to prolong the time the generating material is used to generate water available to humidify respiratory gases relative to an identical generating material present in a similar apparatus in an amount equal to the amount of the generating material and positioned as a layer of uniform thickness across substantially the entire flow path of respiratory gases passing through the housing from the second port.

11. The apparatus of claim 10 wherein the generating material is present in the housing in an amount of less than about 80 grams.

12. The apparatus of claim 10 further comprising a hygroscopic component positioned in the housing and being adapted to generate heat available to heat respiratory gasses passing through the housing.

13. An apparatus for heating and humidifying respiratory gases comprising:

a housing having a first port connected to a tracheal tube device and a second port connected to a tube for passing respiratory gases to and from the housing, the first port and the second port being positioned so that respiratory gases passing to and from the housing pass therebetween;

a gas permeable member positioned in the housing between the first port and the second port and having a size and structure effective to exchange heat and moisture with respiratory gases passing to the housing and with respiratory gases passing from the housing;

a generating material located in the housing between the first port and the second port and being present in an amount effective to generate water available to humidify respiratory gases passing through the housing; and a hygroscopic component positioned in the housing and spaced separate and apart from the gas permeable member and from the generating material and being adapted to generate heat available to heat respiratory gases passing through the housing.

14. The apparatus of claim 13 wherein the generating material is present in the housing in an amount of less than about 80 grams.

* * * * *